United States Patent [19]

Cassidy et al.

[11] Patent Number: 4,515,485

[45] Date of Patent: May 7, 1985

[54] MOLTEN METAL SAMPLE CUP

[75] Inventors: John E. Cassidy, Churchville; L. Raymond Jones, Jr., Huntingdon Valley, both of Pa.

[73] Assignee: Electro-Nite Co., Philadelphia, Pa.

[21] Appl. No.: 459,904

[22] Filed: Jan. 21, 1983

[51] Int. Cl.³ .............................................. G01K 1/08
[52] U.S. Cl. ...................................... 374/157; 374/139
[58] Field of Search ....................... 374/157, 139, 179; 73/DIG. 9

[56] References Cited

U.S. PATENT DOCUMENTS

| Re. 26,409 | 6/1968 | Hance | 73/359 |
|---|---|---|---|
| 3,546,921 | 12/1970 | Bourke et al. | 73/17 |
| 3,844,172 | 10/1974 | Jeric | 374/157 |
| 3,946,594 | 3/1976 | Surinx | 374/26 |
| 3,950,992 | 4/1976 | Hance | 374/157 |
| 4,056,407 | 11/1977 | Cure | 374/157 |
| 4,059,996 | 11/1977 | Cure | 73/354 |
| 4,358,948 | 11/1982 | Plessers | 374/26 |

Primary Examiner—Charles Frankfort
Assistant Examiner—David R. Schuster
Attorney, Agent, or Firm—Seidel, Gonda & Goldhammer

[57] ABSTRACT

A molten metal sample cup is provided with a temperature sensor to detect phase change in molten metal within the cup as the sample solidifies. A blob of material which promotes the formation of carbides is disposed within the cup. The exposed surface of the blob is limited by locating the blob within a recess in a bottom wall of a cavity so that the exposed surface of the blob is a predetermined uniform amount which is less than the total surface of the blob.

15 Claims, 1 Drawing Figure

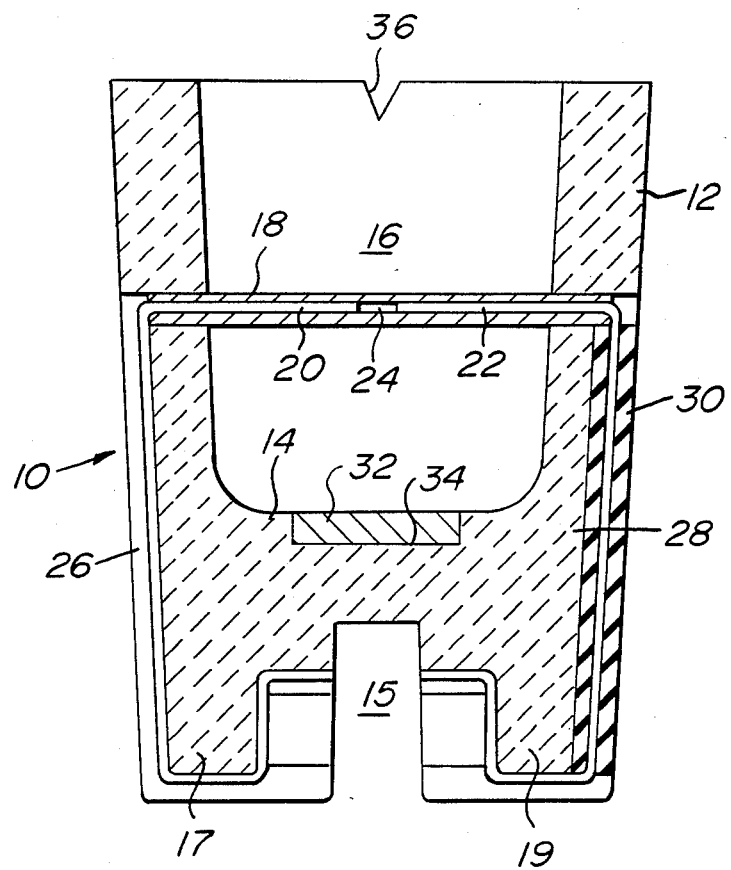

MOLTEN METAL SAMPLE CUP

BACKGROUND OF THE INVENTION

The present invention relates to an improved molten metal sample cup for detecting phase changes, thermal arrest temperatures, and the like of molten metal such as cast iron, steel and the like. Cups of this general type are known. For example, see U.S. Pat. No. Re. 26,409; U.S. Pat. No. 3,546,921; and U.S. Pat. No. 4,059,996.

U.S. Pat. No. 3,546,921 discloses a method of producing an initial thermal arrest in the cooling curve of a molten sample of hypereutecic cast iron by introducing into the sample a stabilizing additive which retards primary graphite formation as the molten sample cools. The stabilizer is added in the form of a pellet or in particulate form. The stabilizing additive is not controlled in any manner with respect to regulating the rate at which the additive is dispersed into the molten metal. As a result, the additive tends to become burned up and not available for white solidification. Further, there is a tendency for the additive to rise to the surface of the molten metal as a slag.

U.S. Pat. No. 4,059,996 sets forth an improvement over the other two patents by disclosing a blob of material in contact with the bottom wall of a cavity. The blob of material includes a carbide formation promoting material mixed with a refractory material and preferably mixed with a material for evolving hydrogen. The refractory material aids in preventing the carbide formation promoting material from being burned up quickly and mixing too quickly with the molten metal. As the size and shape of the blobs differ, so does the surface areas of the blobs differ. The rate at which the additive which promotes the formation of carbides is released into the molten metal is an ever-changing rate that is controlled by the blob surface area which also changes.

In connection with such sample cups, the initial activity of boiling is an uncontrolled happening that influences the final results. It has been found that where boiling is of a minor nature, there is a metal loss of a percent or two. Cups that have greater activity or more pronounced boiling, can result in a metal loss of as much as ten percent. A change in the amount of metal in the sample produced different results when the blobs are of uniform amount.

The present invention is directed to a solution of the problems associated with the prior art and in particular regulation of the dispersion of the additive into the molten iron in a manner which is simple and inexpensive while obtaining more uniformity in results.

SUMMARY OF THE INVENTION

The invention is directed to a molten metal sample cup for use in determining phase change of molten metal. The cup is made from a refractory material and has a cavity for receiving molten metal. A temperature sensing means is provided in the cavity. A blob which includes a material which promotes the formation of carbides is provided in the cavity. A means is provided for limiting the exposed surface of the blob within the cavity to a predetermined uniform amount which is less than the total surface area of the blob.

The last mentioned means is preferably obtained in a manner which is simple and inexpensive. Thus, a recess is provided in the bottom wall of the cup. The recess has uniform transverse dimensions. When the entirety of the blob is disposed within the recess, it presents a predetermined uniform exposed surface to the molten metal.

Various objects and advantages of the present invention will be set forth hereinafter.

For the purpose of illustrating the invention, there is shown in the drawings a form which is presently preferred; it being understood, however, that this invention is not limited to the precise arrangements and instrumentalities shown.

The FIGURE is a vertical sectional view through a sample cup with a blob of material in contact with the inner surface of the cup in accordance with the present invention.

DETAILED DESCRIPTION

Referring to the drawing, there is illustrated a vertical sectional view of a molten metal sample cup in accordance with the present invention and designated generally as 10. The cup is made from a refractory material with an upstanding wall 12 connected at its lower end to a bottom wall 14 to thereby define the sample cavity 16. The bottom wall 14 has a centrally disposed recess 15 thereby delineating support legs or projections 17, 19. Wall 12 may be cylindrical or rectangular.

The cup includes a temperature sensor for sensing the temperature of the sample and facilitating recording of temperature changes on a graph. The temperature sensor preferably includes a protective shield 18 extending diametrically across the cavity 16. The ends of the shield 18 terminate within the wall 12. The shield 18 is annular in cross-section and transparent to radiation. The preferred material for shield 18 is quartz or other comparable materials.

The temperature sensor includes thermocouple wires 20 and 22 partially disposed within shield 18 and connected together at the hot junction 24. Hot junction 24 is adjacent to the central axis of the cavity 16. The materials for the thermocouple wires are conventional and well known to those skilled in the art.

Opposite sides of the cup wall 12 are provided with peripheral grooves 26 and 28. Thermocouple wire 20 extends along groove 26, and then is bent so as to extend into the recess 15 where it may be utilized as a contact portion. The wire 22 extends extends through a protective sleeve 30 disposed within groove 28 and then is bent into the recess 15 where it may likewise constitute a contact portion. The sample cup as thusly described is for illustrated purposes only.

Within the cavity 16, there is provided a blob 32. Blob 32 includes a material which promotes carbide formation in the sample of molten metal. The blob preferably also contains a material for evolving hydrogen when the blob is contacted by molten metal. The hydrogen evolving material promotes more thorough and efficient mixing of the carbide formation promoting material. By mixing a refractory material with carbide formation promoting material, the latter is released and dispersed into the sample of molten metal over a period of time rather than almost instantaneously.

A preferred refractory material for use in forming the blob is a mixture of about 60% silica and about 40% alumina. The term percent means weight percent and is based on the total weight of the blob. The refractory material is conventional, readily available, and may contain small amounts of other metallic oxides. The blob contains refractory material in the amount of about 20% to about 50% of the weight of the blob.

The material for promoting carbide formation and, therefore, white solidification of hypereutectic iron, is a metal selected from the group consisting of bismuth, boron, cerium, lead, magnesium, and tellurium. Tellurium is presently preferred when in crystaline form preferably with crystal sizes of 30 to 150 microns. The preferred crystaline form is a mixture of 2 to 15% with grain size more than 106 microns, 40 to 65% with grain size more than 63 microns, and 70 to 98% with a grain size more than 38 microns. The material for promoting carbide formation is present in the blob in about 10% to about 30% of the weight of the blob.

White solidification of molten iron can be improved with hydrogen. Hydrogen not only accelerates nucleation, but also causes a boiling effect thereby improving the mixing of the carbide formation promoting material in the molten iron. Preferably, hydrogen is evolved from the water of crystalization in water glass which is incorporated in the blob from about 15 to about 50% with the preferred amount being 24%. The preferred amount of water glass or other hydrogen evolving material should be added in an amount so that boiling action is achieved without causing the molten metal to overflow from the cup. The presently preferred water glass has a $SiO_2$ to $Na_2O$ ratio of about 2 to 2.1 and a density of about 50 to about 52 Baume.

To regulate the exposed surface area of the blob 32, the bottom wall 14 is provided with a cavity 34 of uniform depth and uniform transverse dimensions. The volume of the cavity 34 is at least as large as the volume of the blob. The volume of the blob may be less than the volume of the recess 34. The upper surface of the blob should be generally level. The recess 34 results in a predetermined uniform amount of surface area of the blob 32 exposed to the sample of molten metal in the cavity 16 even after a portion of the tellurium has been leeched out and dispersed into the sample.

It has been found desirable to control the amount of metal in the sample that remains in the cup 10 after boiling has subsided. One manner in which this may be accomplished is by providing an overflow notch 36 in the upper edge of the cup 10. By controlling the volume of the sample so that its surface level is at the apex of notch 36, more uniformity of results will be attained.

The present invention may be embodied in other specific forms without departing from the spirit or essential attributes thereof and, accordingly, reference should be made to the appended claims, rather than to the foregoing specification, as indicating the scope of the invention.

I claim:

1. A molten metal sample cup for use in determining phase change of molten metal comprising a refractory cup having a cavity for receiving molten metal, temperature sensing means in said cavity and supported by said cup, a blob which includes a material which promotes the formation of carbides, said blob being disposed within said cavity, and means within said cavity for limiting the surface area of said blob exposed to said cavity to a predetermined uniform amount which is less than one half the total surface of the blob.

2. A cup in accordance with claim 1 wherein said limiting means includes a recess in a wall of said cup, said recess being contiguous with said cavity, said recess having uniform transverse dimensions, and the entirety of said blob being within said recess with one surface thereof exposed to the cavity as defined by the dimensions of said recess.

3. A cup in accordance with claim 2 wherein said cavity is circular and of uniform depth.

4. A cup in accordance with claim 2 wherein said recess is in a bottom wall of said cup.

5. A cup in accordance with claim 4 wherein said blob is a mixture of said material with a refractory and a material for evolving hydrogen when the blob is in contact with molten metal.

6. A cup in accordance with claim 1 including an overflow notch at the upper edge of said cup.

7. A molten metal sample device for use with molten metal comprising a refractory body having a cavity for receiving molten metal, temperature sensing means in said cavity and supported by said body, a blob which includes a material which promotes the formation of carbides, means for limiting the exposed surface area of said blob within said cavity to a predetermined uniform amount which is less than the total surface of the blob, said limiting means including a recess in a bottom wall of said body, said recess being contiguous with said cavity, and the entirety of said blob being within said recess with one surface thereof exposed to the cavity, the area of said exposed surface being defined by the dimensions of said recess.

8. A cup in accordance with claim 7 wherein said cavity is circular and of uniform depth.

9. A cup in accordance with claim 7 wherein the cavity is of uniform transverse dimensions.

10. A molten metal sample device for use with molten metal comprising:
    (a) a refractory body having a cavity for receiving molten metal, temperature sensing means in said cavity and supported by said body,
    (b) a blob containing a mixture of a refractory and a material which which promotes the formation of carbides and a material for evolving hydrogen when the blob contacts molten metal, and
    (c) means for limiting the exposed surface area of said blob to a predetermined uniform amount which is less than the total surface of the blob, said limiting means including a recess in a bottom wall of said body, said recess being contiguous with said cavity, said recess having uniform depth and transverse dimensions, and the entirely of said blob being within said recess with only one surface thereof exposed to the cavity, the area of said exposed surface being predetermined by the dimensions of said recess.

11. In an improved molten metal sample cup for use in determining phase changes of molten metal having a refractory cup with a cavity for receiving molten metal, temperature sensing means supported by said cup and a blob which includes a material which promotes the formation of carbides, said blob being disposed within said cavity wherein the improvement comprises means within said cavity for limiting a prearranged portion of the surface area of said blob exposed to said cavity to a predetermined uniform surface area which is less than one-half the total surface area of the blob.

12. A cup according to claim 11 wherein said limiting means includes a recess in a wall of said cup, said recess being contiguous with said cavity, said recess having uniform transverse dimensions, and the entirety of said blob being within said recess with one surface thereof exposed to the cavity as defined by the dimensions of said recess.

13. A cup in accordance with claim 12 wherein said cavity is circular and of uniform depth.

14. A cup in accordance with claim 12 wherein said recess is in a bottom wall of said cup.

15. A cup in accordance with claim 11 including an overflow notch at the upper edge of said cup.

* * * * *